(12) United States Patent
Wang et al.

(10) Patent No.: US 9,535,061 B1
(45) Date of Patent: Jan. 3, 2017

(54) MULTI-FUNCTIONAL RAPID DIAGNOSTIC TEST DEVICE

(71) Applicant: DNT SCIENTIFIC RESEARCH, LLC, San Diego, CA (US)

(72) Inventors: Naishu Wang, Poway, CA (US); Michael Chang Chien, Cerritos, CA (US)

(73) Assignee: DNT SCIENTIFIC RESEARCH, LLC, San Diego, CA (US)

( * ) Notice: Subject to any disclaimer, the term of this patent is extended or adjusted under 35 U.S.C. 154(b) by 0 days.

(21) Appl. No.: 15/196,459

(22) Filed: Jun. 29, 2016

(51) Int. Cl.
*G01N 33/558* (2006.01)
*G01N 33/543* (2006.01)
*G01N 1/14* (2006.01)

(52) U.S. Cl.
CPC ......... *G01N 33/54386* (2013.01); *G01N 1/14* (2013.01); *G01N 33/558* (2013.01)

(58) Field of Classification Search
None
See application file for complete search history.

(56) References Cited

U.S. PATENT DOCUMENTS

| | | | |
|---|---|---|---|
| 4,299,916 A | 11/1981 | Litman et al. | |
| 4,366,241 A | 12/1982 | Tom et al. | |
| 5,656,503 A | 8/1997 | May et al. | |
| 6,140,136 A | 10/2000 | Lee | |
| 6,403,383 B1 * | 6/2002 | Casterlin | A61B 10/007 422/412 |
| 6,875,185 B2 | 4/2005 | Wong et al. | |
| 7,431,882 B2 * | 10/2008 | Parker | A61B 10/007 422/412 |
| 7,741,103 B2 | 6/2010 | Guirguis | |
| D626,249 S | 10/2010 | Wang et al. | |
| 7,879,623 B2 | 2/2011 | Guirguis | |
| 7,981,382 B2 * | 7/2011 | Wong | A61B 10/0045 422/401 |
| 8,021,625 B2 | 9/2011 | Wang et al. | |
| 8,206,661 B2 * | 6/2012 | Vallejo | A61B 10/007 422/401 |
| 8,889,424 B2 | 11/2014 | Ehrenkranz et al. | |
| 8,916,390 B2 | 12/2014 | Ozcan et al. | |
| 9,377,457 B1 | 6/2016 | Wang et al. | |
| 9,414,813 B2 * | 8/2016 | Engel | A61B 10/0045 |
| 2005/0163660 A1 * | 7/2005 | Wang | B01L 3/502 422/417 |
| 2006/0292700 A1 | 12/2006 | Wang et al. | |
| 2007/0065339 A1 * | 3/2007 | Huff | A61B 10/007 422/400 |
| 2007/0259442 A1 * | 11/2007 | Gould | A61B 10/007 436/165 |

(Continued)

*Primary Examiner* — Chris L Chin
(74) *Attorney, Agent, or Firm* — Innovation Capital Law Group, LLP; Vic Lin

(57) ABSTRACT

A three-in-one apparatus for analyzing liquids, such as some body fluids, uses labeled molecular affinity binding, such as immunochromatography. The multi-functional diagnostic test device can detect an analyte, such as an antibody or antigen, which may indicate a particular condition. The multi-functional diagnostic test device provides multi-functional formats to apply in multiple different sampling methods, including the "dip", "cassette" and "collection" formats. The diagnostic test device can accommodate a plurality of test strips, such as 18 test strips for analyzing up to 90 analytes.

20 Claims, 13 Drawing Sheets

(56) References Cited

U.S. PATENT DOCUMENTS

2013/0022517 A1* 1/2013 Engel ............... A61B 10/0045
                                                    422/408
2015/0173742 A1* 6/2015 Palese ............... A61B 17/0401
                                                    606/144
2015/0211987 A1   7/2015 Burg et al.

* cited by examiner

MULTI-FUNCTIONAL RAPID DIAGNOSTIC TEST DEVICE

BACKGROUND OF THE INVENTION

1. Field of the Invention

One or more embodiments of the invention relate generally to apparatus for analyzing liquids, such as body fluids, using labeled molecular affinity binding, such as immunochromatography. More particularly, the invention relates to a multi-functional strip test apparatus for detecting an analyte, such as an antibody or antigen, which may indicate a particular condition.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Labeled molecular affinity binding, such as immunochromatographic assays, have existed for decades and have proven to be an inexpensive way to screen for various conditions, such as abused drugs, and other conditions, such as pregnancy and cancer, or for single or multiple pathogenic conditions, such as HIV infection.

In the point-of-care test (POCT) setting, immunochromatographic assays are typically conducted using lateral flow strip technology as described in May et al., U.S. Pat. No. 5,656,503, incorporated herein by reference. With lateral flow devices, antibodies are movably supported on a solid support, such as a porous pad. Antigen derivatives are deposited as immobilized indicator lines downstream of the antibodies, whereby the target antigens in a fluid sample flow laterally as a liquid matrix by capillary action through the solid support. The antibodies are normally colored for visual indication. The fluid sample carries the antibodies downstream towards the indicator lines of immobilized antigen derivatives while a reaction takes place between the target antigens and the antibodies. Any antibodies that have not reacted with the antigen in the sample bind to the antigen derivatives at the indicator lines. When little or no target antigen is present in the sample, most or all of the colored antibodies are carried downstream to the indicator lines of the immobilized antigen derivatives. At the immobilized antigen derivatives, the colored antibodies bind together with the antigen derivatives in such concentrations that the colorant of the antibodies becomes readily visible. It is also known that the antigen derivatives' and the antibodies' roles can be interchanged. That is, the antigen derivatives can be labeled with colorant and movably placed in the solid support while the antibodies are placed as immobilized deposited indicator lines downstream.

Unfortunately, although they can be inexpensive and simple-to-use, depending on the type of condition being detected, these tests typically take from about 5 to 20 minutes to complete and provide a typical accuracy of between 75% and 95%, falling short of the 99% or above accuracy generally considered to be necessary for a confirmatory test. Moreover, these conventional tests provide no objective measure of a quantitative result, such as the concentration of a given drug present in the liquid being tested.

The reasons for the insufficient accuracy in many rapid in vitro diagnostic (IVD) test devices are primarily due to their current lack of overall higher sensitivity and specificity. Different samples may contain chemicals or particles which inhibit the rapid and well mixed liquid flow or otherwise interfere with one or both of the first and second affinity binding reactions.

Other prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Moreover, the manufacturing step of pretreating with a second pretreatment chemical can dislodge some of the first pretreatment chemical.

Further, lot-to-lot variation in the manufacture of many IVD test devices can often lead to ambiguous results, such as false negatives as well as weak false positives, so-called "ghostlines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

Depending on the particular test to be performed, the analyte to be detected, or the preference of the user, multiple test devices may be necessary for performing tests in different formats, such as a dip format, a cassette format or a collection format. Each of these test devices may include multiple parts, resulting in confusion, mismatched components, and the like.

Therefore, there is a need to improve the accuracy of rapid IVD test devices so that rapid, inexpensive, easily conducted and quantitative immunological testing becomes a reality and where a single device may be used for multiple test formats.

SUMMARY OF THE INVENTION

Embodiments of the present invention provide a device for testing a liquid sample for the presence of at least one analyte comprising an inner tube; a plurality of test strip slots disposed about an outer periphery of the inner tube, each of the plurality of test strip slots configured to receive a test strip; an outer tube slidably receiving the inner tube in a first end thereof; a squeezing chamber removably attachable to a second, opposite end of the outer tube; and a sample retention chamber disposed on one end of the squeezing chamber.

Embodiments of the present invention further provide a test system for testing a liquid sample for the concentration of at least one analyte comprising at least one test strip comprising a conjugate color pad including a source of mobilizable labeled first affinity binding members bindable to the analyte, a liquid permeable reaction region including at least one strip line including immobilized second affinity capture binding members bindable to said analyte, and a strip compression pad disposed over the conjugate color pad; and a test device comprising an inner tube, a plurality of test strip slots disposed about an outer periphery of the inner tube, each of the plurality of test strip slots configured to receive a test strip, an outer tube slidably receiving the inner tube in a first end thereof, compression pads disposed as raised regions on an interior periphery surface of the outer tube, the compression pads configured to press upon the strip compression pads when the inner tube is inserted into the outer tube, a squeezing chamber removably attachable to a second, opposite end of the outer tube, and a sample retention chamber disposed on one end of the squeezing chamber.

Embodiments of the present invention also provide a method for testing for an analyte in a sample comprising disposing a plurality of test strips into test strip slots configured about an outer periphery of an inner tube, wherein an end portion of each of the plurality of test strips extends beyond an end of the inner tube; sliding the inner tube into an outer tube, where the end portion extends beyond an end of the outer tube; contacting a sampling pad of the plurality of test strips with the sample; and reading the plurality of test strips to determine presence or absence of the analyte.

In some embodiments, the device further comprises a strip line area disposed in the outer tube, the strip line area permitting visible analysis of the test strip received in the plurality of test strip slots.

In some embodiments, the device further comprises fluid directing channel walls disposed on an outer surface of the inner tube and slots disposed on an interior surface of the outer tube, wherein the fluid directing channel walls are received by the slots when the inner tube is slid into the outer tube.

In some embodiments, the device further comprises a flared end on the inner tube, the flared end stopping the inner tube from sliding completely into the outer tube.

In some embodiments, the device further comprises spiral treads disposed about an exterior surface at one end of the outer tube, wherein mating spiral treads on the squeezing chamber mate therewith.

In some embodiments, the device further comprises compression pads disposed as raised regions on an interior periphery surface of the outer tube, wherein the compression pads are configured in a wedge shape.

In some embodiments, the device further comprises one or more stop lines disposed on an outer surface of the inner tube, the stop lines defining an insertion amount of the inner tube inside the outer tube where the compression pads begin to compress on a strip compression pad of the test strips.

In some embodiments, the device further comprises one or more apertures disposed in a central region of the squeezing chamber, the one or more apertures communicating with an interior of the sample retention chamber when the device is assembled, wherein the squeezing chamber includes a fluid collector holder adapted to receive a fluid collector therein.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
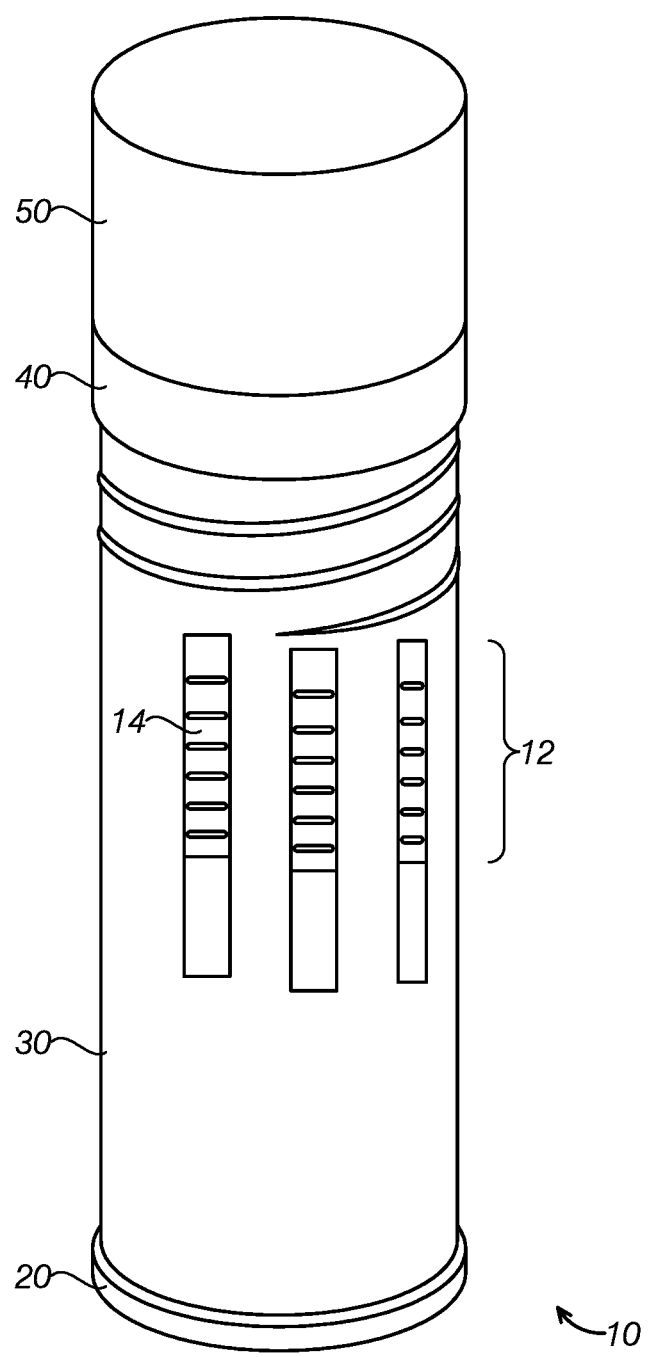
FIG. 1 is a perspective view of a multi-functional diagnostic test device, fully assembled, according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or"

includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

The instant embodiments are useful to rapidly determine the presence of an analyte in a liquid sample at a concentration which confirms the condition being tested. The sample can include, for example, body fluids, such as whole blood, serum, plasma, urine, spinal fluid, amniotic fluid, mucous, saliva, and the like, or other fluids used in certain food and environmental testing.

As used herein, the term "analyte" refers to a compound or composition to be measured. The analyte can be any substance, such as an antigen or ligand, for which there exists a naturally or genetically occurring specific binding member, for instance, a binding molecule such as an antibody or receptor, and other molecules that exhibit the so-called "lock-in-key" pairing function.

Analytes also includes any antigenic substances, haptens, antibodies, and combinations thereof. The analyte can include a protein; a peptide; an amino acid; a ligand; a hormone; asteroid; a vitamin; a drug, including those administered for therapeutic purposes as well as those administered for illicit purposes; a pathogen; and an exogenious infectious microbe, such as a bacterium, a virus, and metabolites of or antibodies to any of the above substances. The analyte can also comprise an antigenic marker or antibody or receptor.

The precise nature of a number of analytes, together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which are herein incorporated by reference in their entirety. Certain improved accuracy devices are disclosed in U.S. Pat. No. 8,021,625 (Wang et al.), which is incorporated herein by reference in its entirety.

The signal provided to the user of the device is provided by accumulation of a visually detectable label conjugated to a mobilizable binding member such as a specific antibody and/or antigen; ligand and/or receptor. This mobilizable binding member is sometimes referred to as a "binding member molecule", "a first affinity binding member", "labeled binding member" or simply "conjugate". In the instant embodiments, labels that produce a readily detectable signal are used. Thus, the instant embodiments provide colored labels which permit visible detection of the assay results without the addition of further substances and/or without the aid of instrumentation. However, in some embodiments, instrumentation may be used to provide a comparative or quantitative representation of the concentration of analyte in the sample.

The test strips described in these embodiments can include regions or pads that may include a dry, porous material. By "porous" it is meant that the matrix of material forming the porous structure allows liquids to flow through it.

As used herein, the term "sample pad" or "fluid collector" means the part of the assay device which is in direct contact with the liquid sample first during test operation, i.e., it receives the sample to be tested for the analyte in question. The fluid collector may be made of porous material, such as porous paper, cotton, cellulose, mixed fibers, glass fiber, polyester fiber, and the like.

The term "conjugate pad" or "conjugate color pad", as used herein, refers to the part of the assay device which is in liquid flow contact with the porous material of fluid collector. The contact can be an overlap or end-to-end connection, such that the liquid sample can migrate via wicking action or by surface tension-based forces such as capillary forces from the fluid collector through the conjugate pad. The conjugate pad comprises a porous material and a mobilizable labeled reagent that is capable of binding the analyte in question to form a labeled reagent-analyte complex which then migrates via liquid flow with the liquid sample along the pad.

The term "mobilizable" as referred to herein means diffusively or non-diffusively attached, or impregnated. The mobilizable reagents are capable of dispersing with the liquid sample and carried by the liquid sample in the liquid flow.

In one exemplary embodiment, human immunodeficiency virus ("HIV") in a fluid specimen, such as saliva, is detected as a putative target analyte. Those skilled in the art will readily appreciate adaptation of these embodiments to detect other analytes indicative of other pathogens, or pathogenic conditions in body, drugs of abuse ("DOA"), food or environmental fluid specimens, and the like.

Further the exemplary embodiments will be described in connection with an immunochromatographic assay based on antigen/antibody binding. Those skilled in the art will readily appreciate adaptation of these embodiments to other types of molecular affinity binding-based tests.

Broadly, embodiments of the present invention provide a three-in-one apparatus for analyzing liquids, such as some body fluids, using labeled molecular affinity binding, such as immunochromatography. The multi-functional diagnostic test device can detect an analyte, such as an antibody or antigen, which may indicate a particular condition. The multi-functional diagnostic test device provides multi-functional formats to apply in multiple different sampling methods, including the "dip", "cassette" and "collection" formats. The diagnostic test device can accommodate a plurality of test strips, such as 18 test strips for analyzing up to 90 analytes.

Referring to FIG. 1, a diagnostic test device 10 can include an inner tube 20, an outer tube 30 fitting over and slidably engageable with at least a portion of the inner tube 20, a squeezing chamber 40 fitting on one end of the outer tube 30, and a sample retention chamber 50 fitting on one end of the squeezing chamber 40.

The outer tube 30 can include a plurality of strip line areas 12. The strip line areas 12 provide visual access to at least a portion of a test strip 14 mounted on the inner tube 20, as described in greater detail below. The number of strip line areas 12 can vary, depending on the number of test strips 14 that mount on the inner tube 20. Typically, from about three to about 30 test strips 14 may be mounted on the inner tube 20, resulting in the same number of strip line areas 12. As an exemplary embodiment, eighteen strip line areas 12 can be provided to permit access to view eighteen test strips 14 mounted on the inner tube 20.

Figure 2A:
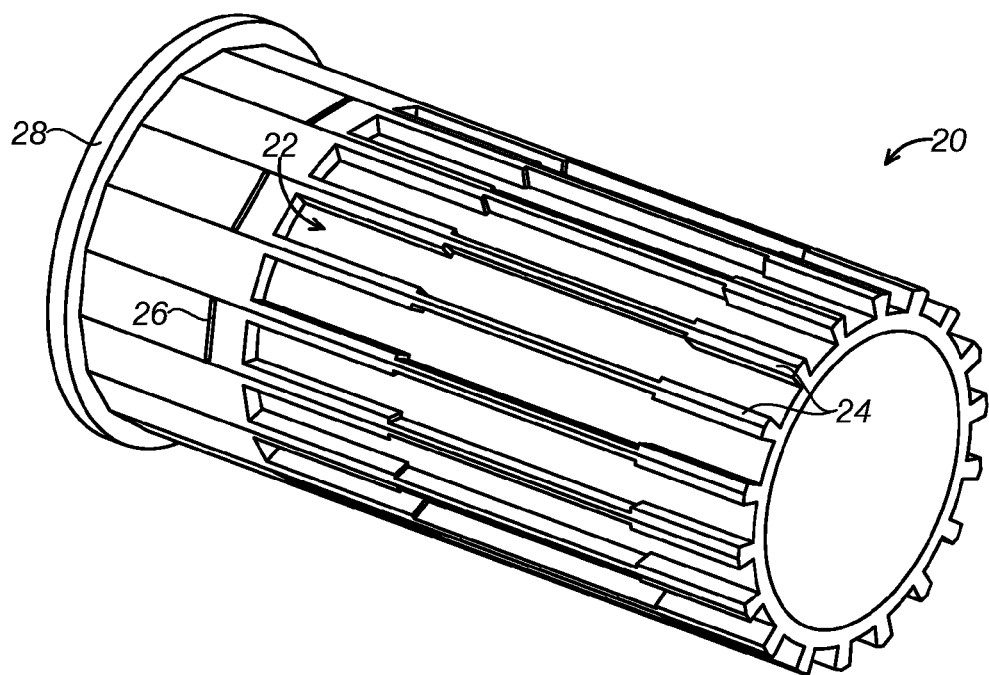
FIG. 2A is a perspective view of an inner tube of the multi-functional diagnostic test device of FIG. 1.
Figure 2B:
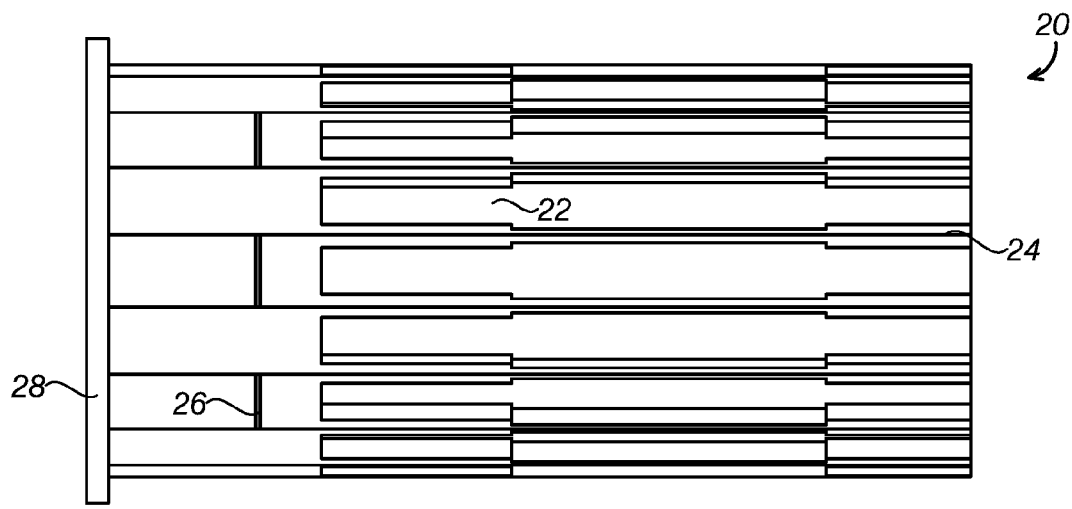
FIG. 2B is a side view of the inner tube of FIG. 2A.
Figure 2C:
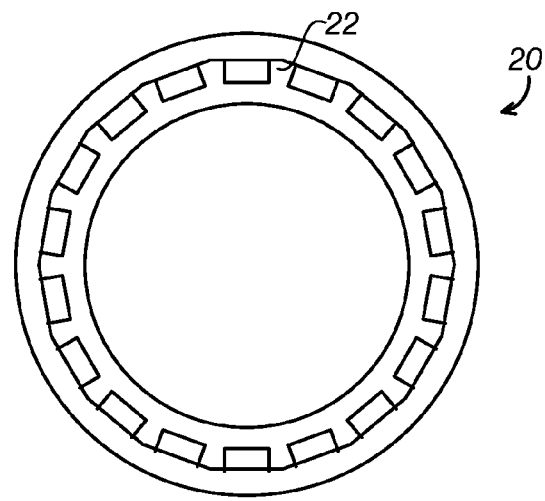
FIG. 2C is a bottom view of the inner tube of FIG. 2A.

Referring to FIGS. 2A through 2C, the inner tube 20 can include a plurality of test strip slots 22 for receiving the test strips 14 therein. Fluid directing channel walls 24 may be disposed between the test strip slots 22. In some embodiments, portions of the fluid directing channel walls 24 may have varying thicknesses for assisting in the retention of the test strips 14 therein. Various configurations of the fluid directing channel walls 24 are contemplated within the scope of the present invention, provided that then secure the test strips 14 and permit compression pads 32 (see FIG. 3A), as described below, to fit therebetween.

One or more stop bars 26 may be disposed at a particular distance from a flared end 28 of the inner tube 20. The stop bars 26 may be positioned at a location where, when the inner tube 20 is inserted into the outer tube 30, the stop bars 26 become hidden behind the outer tube 30 as the compression pads 32 press on a conjugated color pad 13 (see FIG. 7) of the test strip 14. The details of this action are described in greater detail below with reference to FIG. 7.

Figure 3A:
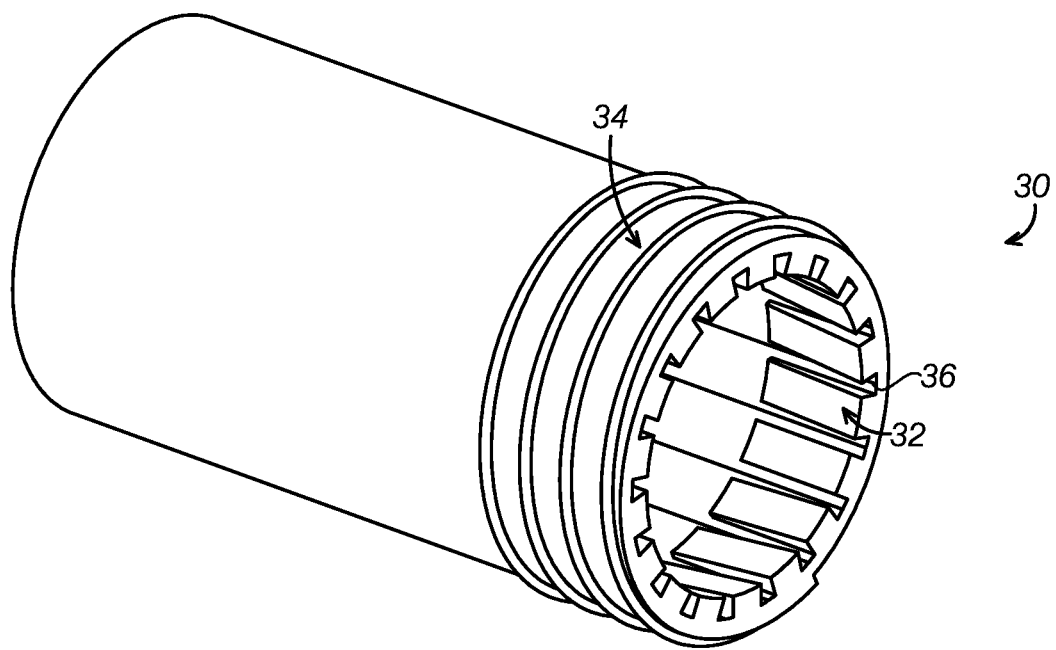
FIG. 3A is a perspective view of an outer tube of the multi-functional diagnostic test device of FIG. 1.
Figure 3B:
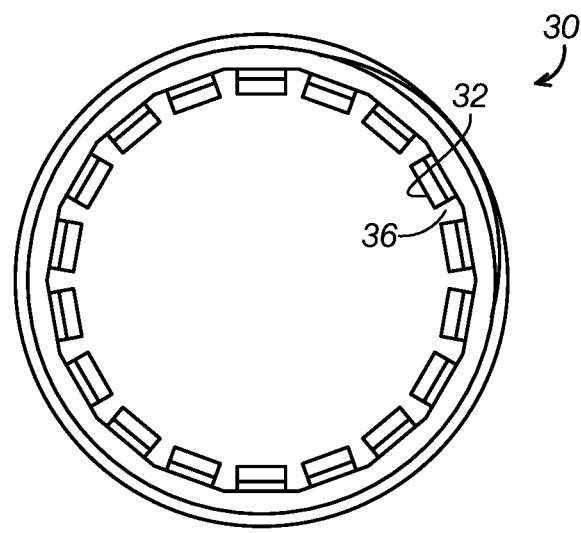
FIG. 3B is a top view of the outer tube of FIG. 3A.
Figure 3C:
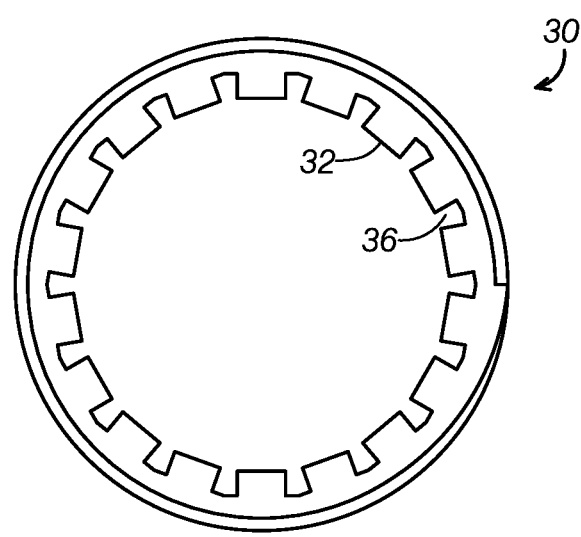
FIG. 3C is a bottom view of the outer tube of FIG. 3A.
Figure 4A:
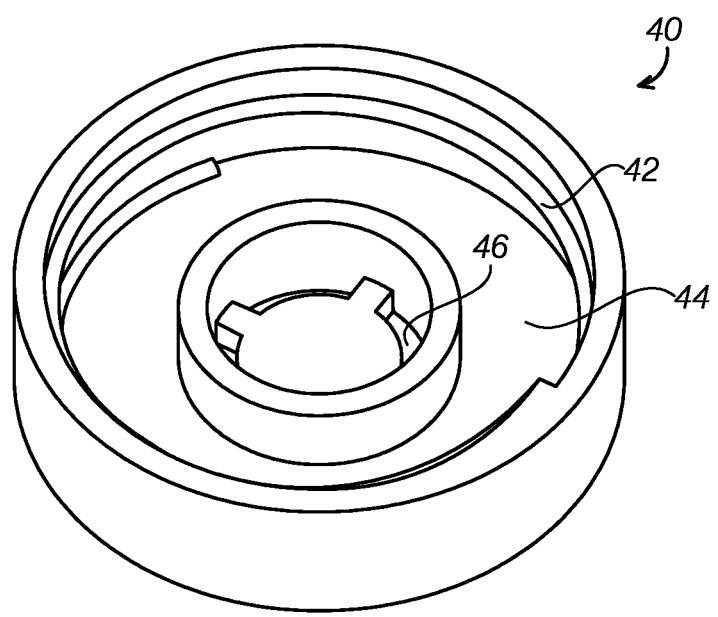
FIG. 4A is a perspective view of a squeezing chamber of the multi-functional diagnostic test device of FIG. 1.
Figure 4B:
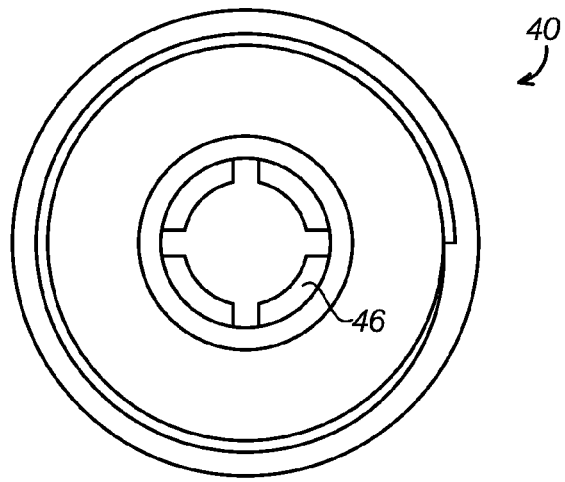
FIG. 4B is a top view of the squeezing chamber of FIG. 4A.
Figure 4C:
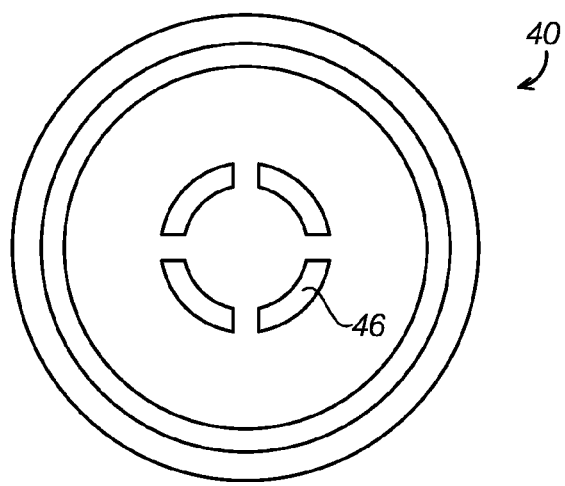
FIG. 4C is a bottom view of the squeezing chamber of FIG. 4A.
Figure 4D:
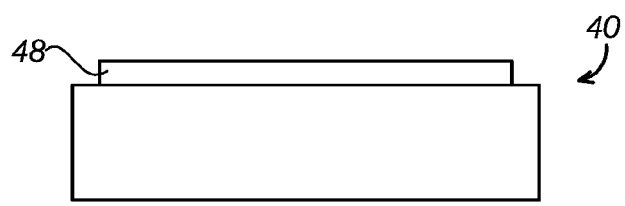
FIG. 4D is a side view of the squeezing chamber of FIG. 4A.
Figure 7:
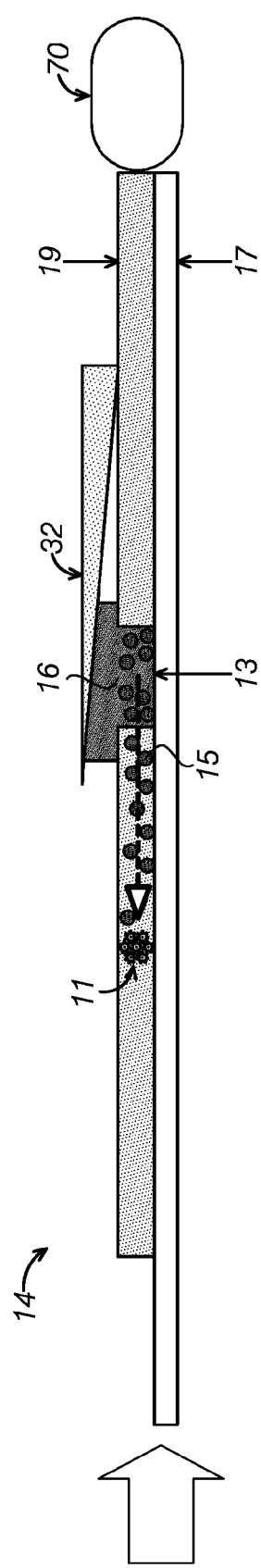
FIG. 7 is a side view illustrating how the test strip of FIG. 6 interacts with a compression pad from the outer tube during use in a collection format.

Referring now to FIGS. 3A through 3C, the outer tube 30 can include the compression pads 32 formed along an inner periphery thereof. Typically, the compression pads 32 are formed in one end of the outer tube 30, separated by slots 36 adapted to receive the fluid directing channel walls 24 therein. The compression pads 32 may be formed in various shapes. Typically, the compression pads 32 are wedge shaped, as best shown in FIG. 7. The compression pads 32 may extend into the outer tube 30 from about 2 percent to about 20 percent of the length of the outer tube 30.

Spiral treads 34 may be disposed on an outer periphery of the outer tube 30 at the same end as the compression pads 32. The spiral treads 34 may be configured to secure the squeezing chamber 40 to the end of the outer tube 30 as shown in FIG. 1.

Referring to FIGS. 4A through 4D, the squeezing chamber 40 can include spiral treads 42 that mate with the spiral treads 34 of the outer tube 30 to permit the squeezing chamber 40 to be removably attached to the outer tube 30. While spiral treads 34, 42 are shown in the Figures and described, various other removable connections are contemplated within the scope of the present invention.

A fluid collector holder 44 may be disposed within the squeezing chamber for containing a sample, as described below. Apertures 46 may be disposed in a central region of the squeezing chamber for permitting fluid to move therethrough.

A connecting ring 48 may be disposed on one end of the squeezing chamber 40. The connecting ring 48 can allow the sample retention chamber 50 to removably attach to the squeezing chamber 40, as shown in FIG. 1, via a friction fit. Other connection mechanisms, while not shown, may be used to removably attach the squeezing chamber 40 to the sample retention chamber 50.

Figure 5:
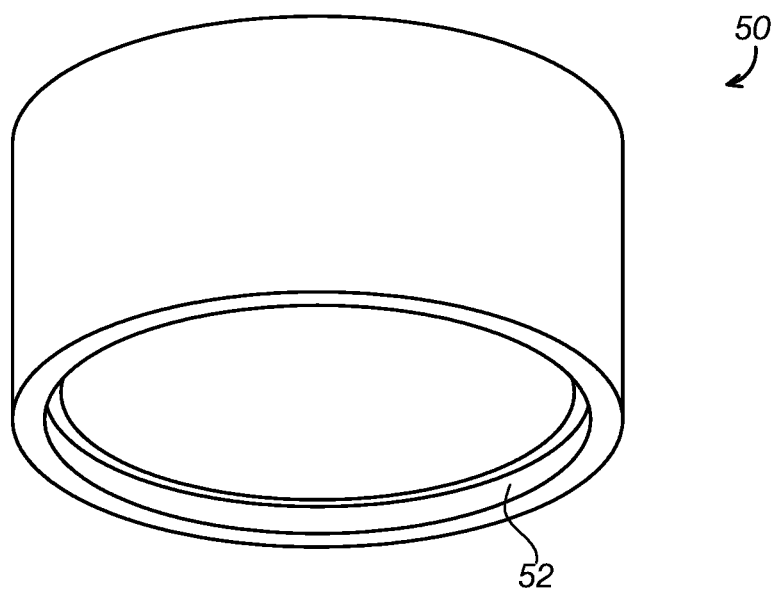
FIG. 5 is a perspective view of a sample retention chamber of the multi-functional diagnostic test device of FIG. 1.

Referring to FIG. 5, the sample retention chamber 50 may be removably attachable to the squeezing chamber 40, as shown in FIG. 1. The sample retention chamber 50 can receive fluid moved through the apertures 46 of the squeezing chamber 40, as described in greater detail below.

Figure 6:
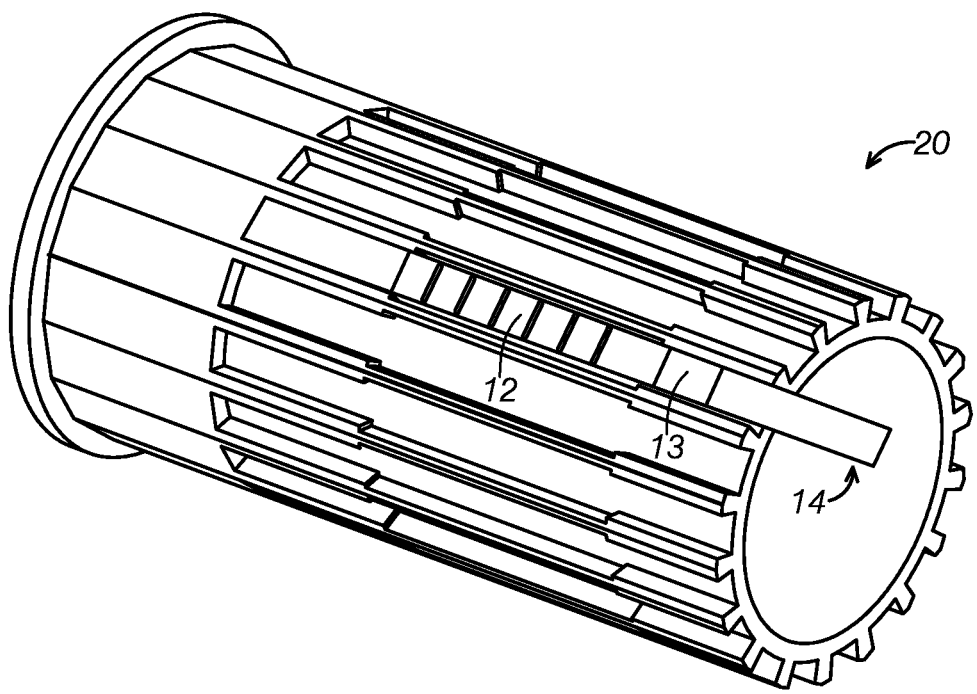
FIG. 6 is a perspective view of the inner tube of FIG. 2A, illustrating a test strip disposed therein.

Referring now to FIGS. 6 and 7, when the test strip 14 is disposed within the inner tube 20 and the inner tube 20 is slid into the outer tube 30, the compression pad 32 from the outer tube 30 may press into a strip compression pad 16 to drive chemical mixtures pre-impregnated on the conjugated color pad 13 out of the conjugated color pad 13 completely. In some embodiments, this design can provide a more predictable rate of uptake of labeled analytes at the strip lines in order to provide a quantitative result.

A fluid collector 70, such as a sponge-like material, may be disposed in the fluid collection holder 44 of the squeezing chamber 40. As the inner tube 20 is slid into the outer tube 30, the fluid collector 70 squeezes fluid onto the sampling pad 19, disposed on the substrate 17, of the test strip 14. As the inner tube 20 is moved further (where the stop lines 26, described above, are no longer visible), the compression pad 32 presses on the strip compression pad 16. The chemical mixtures 15 move forward and the reaction components 11 may be trapped on strip lines (not specifically shown) as is known in the test strip art.

Figure 8:
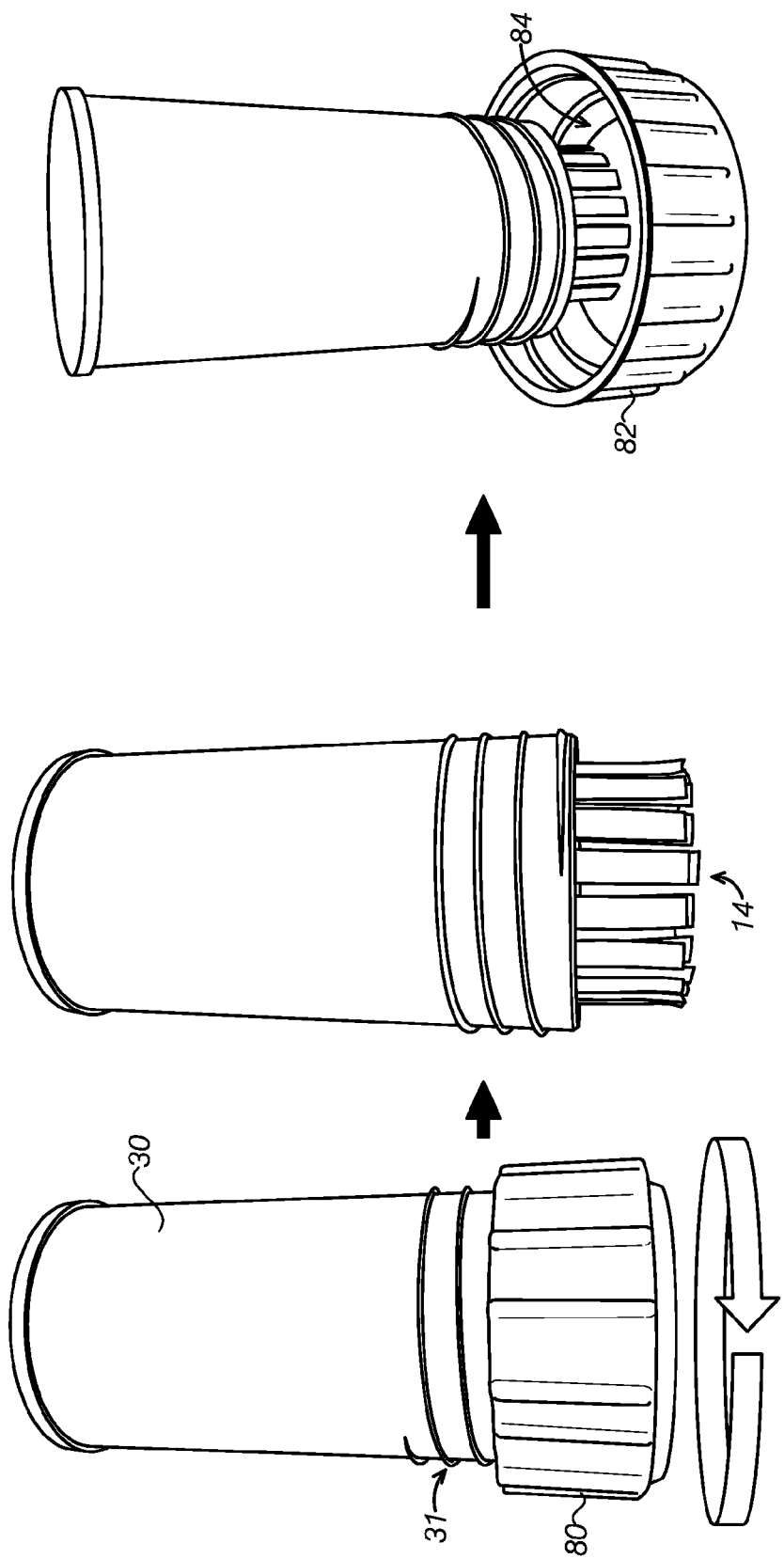
FIG. 8 is a pictorial representation illustrating the multi-functional diagnostic test device being used in a dip format.

In a traditional dip format of diagnostic testing, multiple test strips are assembled in a planar format. When the test strip number is over 10, test strips are typically assembled in a double-sided format to avoid the uneven dipping due to the width. Referring to FIG. 8, in the present invention, a plurality of test strips 14 can be arranged in one peripheral plane, allowing the dipping to be easy and more even than traditional methods.

In this embodiments, the test strips 14 may be arranged about the inner tube 20 and the inner tube may be fully inserted into the outer tube 30. A cap 80 may attach to the bottom of the outer tube 30 via, for example, the spiral treads 34. Removal of the cap 80 may expose the sampling pads 19 of the test strips 14. A container 82 containing sample 84 may be disposed on a surface and the test strips 14, exposed after removing the cap 80, may be placed into the sample 84 for a period of time suitable for performing the test. The cap 80 may be a separate item, or may simply be formed from the assembly of the squeezing chamber 40 and the sample retention chamber 50.

In some embodiments, the sample 84 may flow up the test strip 14 via absorption. In other embodiments, the inner tube 20 may not be fully inserted into the outer tube 30 when the "dip" is performed. Once the sample 84 reaches the conjugate color pad 13, the inner tube 20 may be fully inserted into the outer tube 30, creating a driven flow via the compression pad 32 and the strip compression pad 16.

In a traditional cassette format of diagnostic testing, test strips are sampled by using a dropper to carry body fluid samples to individual strips, typically requiring 3-4 droplets of sample per test strip. This takes significant time, especially when multiple strips are being tested. In some cases, over-dropping fluid will flow into the cassette and cause a testing failure.

Figure 9:
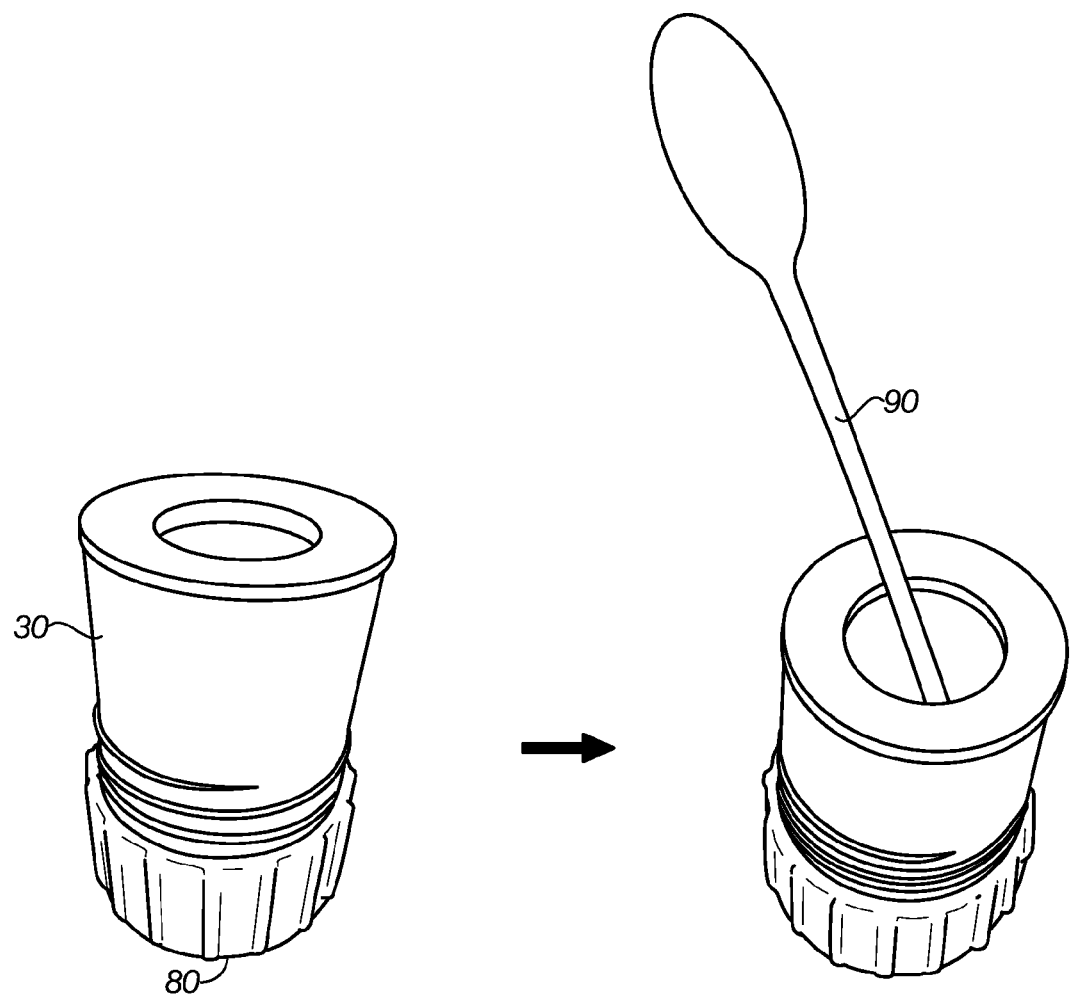
FIG. 9 is a pictorial representation illustrating the multi-functional diagnostic test device being used in a cassette format.

Referring to FIG. 9, a cassette format of testing can use a certain amount of sample fluid, such as 5 mL, for example, which is transferred, such as via pipette 90, directly through the inner tube 20 and retained in the sample retention chamber 50 (or cap 80, as shown). Multiple test strips 14 can absorb body fluid evenly with almost the same amount of body fluid for each test strip. By his particular sampling method, there is no chance to get testing failure due to the test strip being overflowed by inappropriate sampling methods.

Referring now to FIGS. 10A through 10D, when body fluid becomes difficult to be collected, it can be taken by the fluid collector 70, which is secured within the squeezing chamber 40. The body fluid can later be squeezed out of the fluid collector 70 for testing. The material of the fluid collector 70 can be any material with an absorption property, such as a sponge.

Figure 10D:
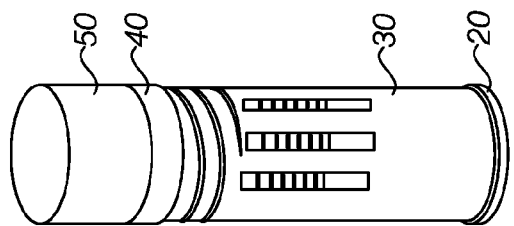
FIG. 10D is a perspective view illustrating the fully closed, collection format multi-functional diagnostic test device, as the test is completed.
Figure 10C:
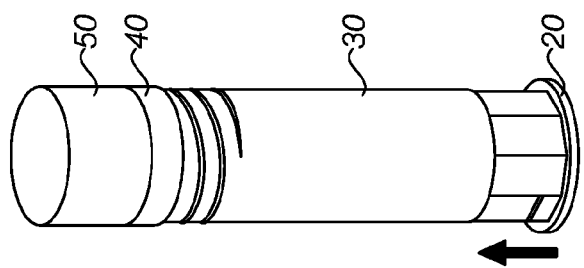
FIG. 10C is a perspective view illustrating a step of pushing the inner tube to begin a test in the collection format using the multi-functional diagnostic test device.
Figure 10B:
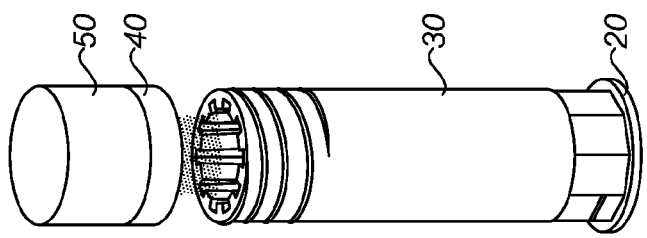
FIG. 10B is a perspective view illustrating a step of closing the collector to the outer tube in performing a test in the collection format using the multi-functional diagnostic test device.
Figure 10A:
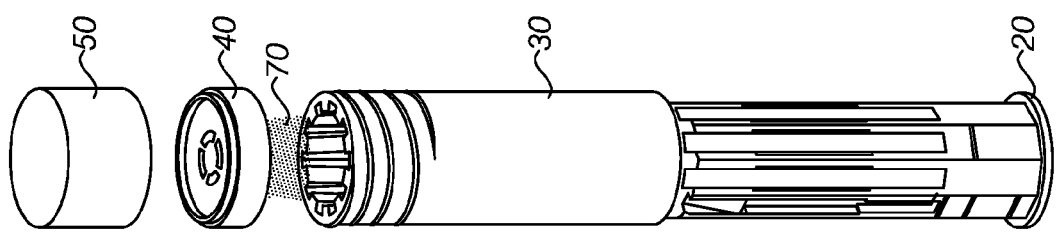
FIG. 10A is an exploded perspective view illustrating the components of the multi-functional diagnostic test device being used in a collection format.

After collecting the body fluid, the squeezing chamber 40 and the sample retention chamber 50 are secured to the outer tube 30 as shown in FIG. 10B. Next, as shown in FIG. 10C, the inner tube is pushed to the end to squeeze the fluid collector and start the testing. As shown in FIG. 10D, the testing occurs and, after about 1 minute, the results may be read. To read the results, the user may read the test strips 14 through the outer tube 30 (which may be, for example, made of a transparent material or include transparent windows), or the user may remove the inner tube 20 from the outer tube 30 and read the results on the test strips 14.

In summary, embodiments of the present invention provide a multi-functional device that can be used in dip, cassette and collection formats. In the dip format, only the inner tube 20, the outer tube 30 and the sample retention chamber 50 (or the cap 80) are used. In the dip format, the device is simply dipped into body fluid that is pre-collected in the container 82. In the cassette format, the same components as the dip format are used, however, the body fluid is dropped into the sample retention chamber 50 (or the cap 80) through the inner tube 20. Finally, in the collection format, all the components are used. In the collection format, excess body fluid can be squeezed into the sample retention chamber 50 via the apertures 46 of the squeezing chamber 40. The sample retention chamber 50 can then be sealed and used for confirmation tests, as required.

In some embodiments, a mobile communication device, such as a smart phone, may be used, as disclosed in Ozcan et al., U.S. Pat. No. 8,916,390, incorporated herein by reference, to automatically scan one or more of the test strips via the camera of a smart phone. The scanned image can then be interpreted by software to obtain a result and deliver that result to a wireless network, for example.

Depending on the analyte being tested and the condition of the fluid specimen, many of the above embodiments have been found to achieve an accuracy of at least 99.99%.

In addition, because a result is obtained so quickly, typically within 1 minute, the test does not require additional buffers or other methods to halt the reaction.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A device for testing a liquid sample for the presence of at least one analyte, comprising:
   an inner tube;
   a plurality of test strip slots disposed about an outer periphery of the inner tube, each of the plurality of test strip slots configured to receive a test strip;
   an outer tube slidably receiving the inner tube in a first end thereof;
   a squeezing chamber removably attachable to a second, opposite end of the outer tube; and
   a sample retention chamber disposed on one end of the squeezing chamber.

2. The device of claim 1, further comprising a strip line area disposed in the outer tube, the strip line area permitting visible analysis of the test strip received in the plurality of test strip slots.

3. The device of claim 1, further comprising:
   fluid directing channel walls disposed on an outer surface of the inner tube; and
   slots disposed on an interior surface of the outer tube, wherein
   the fluid directing channel walls are received by the slots when the inner tube is slid into the outer tube.

4. The device of claim 1, further comprising a flared end on the inner tube, the flared end stopping the inner tube from sliding completely into the outer tube.

5. The device of claim 1, further comprising spiral treads disposed about an exterior surface at one end of the outer tube, wherein mating spiral treads on the squeezing chamber mate therewith.

6. The device of claim 1, further comprising compression pads disposed as raised regions on an interior periphery surface of the outer tube.

7. The device of claim 6, wherein the compression pads are configured in a wedge shape.

8. The device of claim 6, further comprising one or more stop lines disposed on an outer surface of the inner tube, the stop lines defining an insertion amount of the inner tube inside the outer tube where the compression pads begin to compress on a strip compression pad of the test strips.

9. The device of claim 1, further comprising one or more apertures disposed in a central region of the squeezing chamber, the one or more apertures communicating with an interior of the sample retention chamber when the device is assembled.

10. The device of claim 1, wherein the squeezing chamber includes a fluid collector holder receiving a fluid collector therein.

11. A test system for testing a liquid sample for the concentration of at least one analyte, comprising:
    at least one test strip comprising:
      a conjugate color pad including a source of mobilizable labeled first affinity binding members bindable to the analyte;
      a liquid permeable reaction region including at least one strip line including immobilized second affinity capture binding members bindable to said analyte; and
      a strip compression pad disposed over the conjugate color pad; and
    a test device comprising:
      an inner tube;
      a plurality of test strip slots disposed about an outer periphery of the inner tube;
      an outer tube slidably receiving the inner tube in a first end thereof;
      compression pads disposed as raised regions on an interior periphery surface of the outer tube, the compression pads pressing upon the strip compression pads when the one of the at least one test strip is placed into one of the plurality of test strip slots and the inner tube is inserted into the outer tube;
      a squeezing chamber removably attachable to a second, opposite end of the outer tube; and
      a sample retention chamber disposed on one end of the squeezing chamber.

12. The test system of claim 11, further comprising a strip line area disposed in the outer tube, the strip line area permitting visible analysis of the test strip received in the plurality of test strip slots.

13. The test system of claim 11, further comprising:
    fluid directing channel walls disposed on an outer surface of the inner tube; and
    slots disposed on an interior surface of the outer tube, wherein
    the fluid directing channel walls are received by the slots when the inner tube is slid into the outer tube.

14. The test system of claim 11, wherein the compression pads are configured in a wedge shape.

15. The test system of claim 11, further comprising one or more stop lines disposed on an outer surface of the inner tube, the stop lines defining an insertion amount of the inner tube inside the outer tube where the compression pads begin to compress on a strip compression pad of the test strips.

16. The test device of claim 11, further comprising one or more apertures disposed in a central region of the squeezing chamber, the one or more apertures communicating with an interior of the sample retention chamber when the device is assembled, wherein the squeezing chamber includes a fluid collector holder receiving a fluid collector therein.

17. A method for testing for an analyte in a sample, comprising:
    disposing a plurality of test strips into test strip slots disposed about an outer periphery of an inner tube, wherein an end portion of each of the plurality of test strips extends beyond an end of the inner tube;
    sliding the inner tube into an outer tube, where the end portion extends beyond an end of the outer tube;
    contacting a sampling pad of the plurality of test strips with the sample; and reading the plurality of test strips to determine presence or absence of the analyte.

18. The method of claim 17, further comprising dipping the sampling pads of the plurality of test strips into the sample that is already placed into a container.

19. The method of claim 17, further comprising
    placing a cap over the end of the outer tube, covering the end portions of each of the plurality of test strips; and
    delivering the sample to an inside of the cap via an interior of the inner tube.

20. The method of claim 17, further comprising:
    placing the sample on a fluid collector disposed in a squeezing chamber attached to the end of the outer tube;
    pushing the inner tube fully into the outer tube to cause the sample to transfer to the sampling pads, and to further cause compression pads, extending from an interior periphery of the outer tube, to press onto strip compression pads, disposed over a conjugate color pad of the plurality of test strips.

* * * * *